(12) United States Patent
Zhang (10) Patent No.: US 6,566,107 B1
(45) Date of Patent: May 20, 2003

(54) RECOMBINANT ZYMOMONAS MOBILIS WITH IMPROVED XYLOSE UTILIZATION

(75) Inventor: Min Zhang, Lakewood, CO (US)

(73) Assignee: Midwest Research Institute, Kansas City, MO (US)

( * ) Notice: Subject to any disclaimer, the term of this patent is extended or adjusted under 35 U.S.C. 154(b) by 0 days.

(21) Appl. No.: 09/704,153

(22) Filed: Nov. 1, 2000

(51) Int. Cl.[7] .................................................. C12P 7/06
(52) U.S. Cl. ......................... 435/161; 435/41; 435/61; 435/194; 435/233; 435/243; 435/252.3; 435/455
(58) Field of Search ............................ 435/41, 61, 455, 435/194, 233, 243, 252.3

(56) References Cited

U.S. PATENT DOCUMENTS

| | | | |
|---|---|---|---|
| 4,403,034 A | 9/1983 | Rogers et al. | 435/161 |
| 5,000,000 A | 3/1991 | Ingram et al. | 435/161 |
| 5,028,539 A | 7/1991 | Ingram et al. | 435/161 |
| 5,041,378 A | 8/1991 | Drummond et al. | 435/234 |
| 5,168,056 A | 12/1992 | Frost | 435/172.3 |
| 5,272,073 A | 12/1993 | Frost et al. | 435/155 |

FOREIGN PATENT DOCUMENTS

WO  WO 92/10561  *  6/1992

OTHER PUBLICATIONS

Feldmann et al., 1992, Appl. Microbiol. Biotechnol. 38:354–361.

* cited by examiner

Primary Examiner—Nashaat T. Nashed
Assistant Examiner—Christian L Fronda
(74) Attorney, Agent, or Firm—Paul J. White (57) ABSTRACT

A strain derived from Zymomonas mobilis ATCC31821 or its derivative capable of producing ethanol upon fermentation of a carbohydrate medium containing xylose to provide enhanced xylose utilization and enhanced ethanol process yield, the strain or its derivative comprising exogenous genes encoding xylose isornerase, xylulokinase, transaldolase and transketolase, the genes are fused to at least one promotor recognized by Zymomonas which regulates the expression of at least one of the genes.

13 Claims, 6 Drawing Sheets

FIG.2B 1.5% Glucose and 3.5% Xylose

FIG. 2C

ZM4 (pZB5): 1.5% Glucose and 3.5% Xylose

RECOMBINANT *ZYMOMONAS MOBILIS* WITH IMPROVED XYLOSE UTILIZATION

CONTRACTUAL ORIGIN OF THE INVENTION

The United States Government has rights in this invention pursuant to Contract No. DE-AC36-99GO10337 between the United States Department of Energy and the Midwest Research Institute.

FIELD OF THE INVENTION

This invention relates to a recombinant *Zymomonas mobilis* strain, bearing xylose and assimilation and pentose-phosphate pathway genes, having improved fermentation performance on xylose or a mixture of glucose and xylose, useful for the fermentation of the pentoses along with glucose in agricultural and cellulosic biomass to ethanol.

This invention also relates to a method which is facile and effective for constructing improved recombinant Zymomonas strains ATCC31821/pZB5. This invention also relates to the process of using ATCC31821/pZB5 strain for rapid and efficient fermentation of the pentose components in agricultural and cellulosic biomass to ethanol. This invention has a significant impact in decreasing the cost of ethanol production from agricultural and cellulosic biomass feedstocks.

BACKGROUND OF THE INVENTION

Cellulosic biomass is a favorable feedstock for fuel ethanol production because it is both readily available and less expensive than either corn or sugarcane. However, substantial hurdles must be overcome before a typical cellulosic feedstock can be utilized effectively as a substrate for the fermentative production of ethanol. The typical feedstock is comprised of approximately 35%–45% cellulose, 30–40% hemicellulose, 15% lignin and 10% of other components. The cellulose fraction is comprised of polymers of the hexose sugar, glucose. The hemicellulose fraction is comprised mostly of pentose sugars, and substantially of xylose.

Whereas microorganisms are known that can efficiently ferment the glucose component in cellulose, conversion of the xylose in the hemicellulose fraction to ethanol has been difficult and this remains to be one of the economical bottlenecks in the biomass to ethanol conversion scheme. The rapid and efficient utilization of the xylose components in cellulosic biomass is desirable in the development of a commercial process.

*Zymomonas mobilis* is a bacterium that has been utilized as a natural fermentative agent in the production of alcoholic beverages, such as pulque and palm wines produced from plant saps. Comparative performance trials have suggested that Zymomonas may become an important industrial ethanol-producing microorganism because of its 5–10% higher yield and up to 5-fold higher productivity compared to traditional yeast fermentations. Because of its potential value, several processes based on the use of Zymomonas for production of industrial ethanol from glucose-based feedstocks have been disclosed in U.S. Pat. Nos. 4,731,329, 4,812,410, 4,816,399, and 4,876,196.

While Zymomonas may become an important fuel ethanol-producing microorganism from glucose-based feedstocks, its substrate utilization range is restricted to fermentation of glucose, sucrose and fructose and, as such, it is not naturally suited for fermentation of the xylose and arabinose components in cellulosic feedstocks. Zymomonas contains the Enter-Douderoff pathway that allows it to ferment glucose very efficiently to ethanol as the sole fermentation product. However, Zymomonas is naturally unable to ferment the xylose in cellulosic biomass because it lacks the essential pentose metabolism pathways. Thus, an opportunity exists to genetically engineer this organism for the fermentation of xylose to ethanol.

Genetic engineering attempts have been made to enhance ethanol production by fermentation by transferring genes from one species to another. For example, see U.S. Pat. Nos. 5,000,000 and 5,028,539. Gene cloning and expression of various enzymes including enzymes for creating a new metabolic pathway are also known. For example see U.S. Pat. Nos. 5,272,073, 5,041,378, 5,168,056 and 5,226,475. However, none of these discoveries has successfully broadened the fermentable substrate range of a microorganism which could not previously ferment pentose sugars to ethanol.

Previous attempts to introduce a pentose catabolic pathway from either Xanthomonas or Klebsiella into Zymomonas have been unsuccessful and the recombinant strains were incapable of growth on xylose as the sole carbon source (Feldmann et al., 1992, Appl. Microbiol. Biotechnol. 38:354–361; Liu et al., 1988. J. Biotechnol. 7:61–77).

The wild-type *Z. mobilis* ferments only glucose, sucrose and fructose and is not able to utilize xylose. Enzymatic analysis indicated that *Z. mobilis* lacks functional pentose metabolic pathways necessary to ferment xylose. The xylose-fermenting *Z. mobilis* has been developed by introduction and expression of four genes encoding xylose-assimilating enzymes, xylose isomerase and xylulokinase as well as pentose-phosphate pathway enzymes, transaldolase and transketolase (Picataggio et al., U.S. Pat. No. 5,514,583).

Despite the success of development of xylose-fermenting Zymomonas strains, the xylose utilization rate is much slower as compared to glucose and often residual xylose is left unfermented under fermentation conditions when the pH is not controlled, or at high sugar concentrations, resulting in lower ethanol productivities and process yields.

SUMMARY OF THE INVENTION

One object of the present invention is to provide a new recombinant xylose-fermenting *Zymomonas mobilis* ATCC31821/pZB5 with improved fermentation performance on xylose or on a mixture of glucose and xylose.

Another object of the present invention is to provide an efficient method to transform the strain ATCC31821 at greater than 1000 CFU/$\mu$g DNA through the use of a methylation-deficient host such as *E. coli* JM110.

A further object of the present invention is to provide a process for use of the recombinant strain ATCC31821/pZB5 to ferment 5% xylose without pH control at about 30° C. with a higher xylose utilization rate to obtain about a 12% increase of fermentation performance of xylose utilization compared to the previous strain CP4(pZB5).

A still further object of the present invention is to provide a process for use of the recombinant strain ATCC31821/pZB5 to ferment 1.5% glucose and 3.5% xylose without pH control that utilizes xylose almost completely (99%) in about 69 hours at about 30° C. to obtain about an 18% increase of fermentation performance of xylose utilization compared to the previous strain CP4 (pZB5) which utilizes only about 84% of the xylose under the same conditions, thus resulting in a 12% increase of the ethanol process yield; and to also provide a 20% increase in average volumetric productivity and a 49% increase in xylose sugar up take rate and a 21% increase in total sugar up take rate using Zymomonas strain ATCC31821/pZB5 compared to the previous strain CP4(pZB5).

A further object yet still of the present invention is to provide a process for use of the recombinant strain ATCC31821/pZB5 to ferment 5% xylose without pH control at about 37° C. with a higher xylose utilization rate to obtain about a 34% increase of fermentation performance of xylose utilization compared to the previous strain CP4(pZB5), thus resulting in a 28% increase of the ethanol process yield; and to also provide a 25% increase in average volumetric productivity and a 28% increase in xylose sugar up take using Zymomonas strain ATCC31821/pZB5 compared to the previous strain CP4(pZB5).

Another object of the present invention is to provide a process for use of the recombinant strain ATCC31821/pZB5 to ferment 1.5% glucose and 3.5% xylose without pH control that utilizes xylose nearly completely (96%) in about 69 hours at about 37° C. to obtain about an 18% increase of fermentation performance of xylose compared to the previous strain CP4 (pZB5) under the same conditions, thus resulting in a 13% increase of the ethanol process yield; and to also provide an 18% increase in average volumetric productivity and a 40% increase in xylose sugar up take rate and a 20% increase in total sugar up take rate using Zymomonas strain ATCC31821/pZB5 compared to the previous strain CP4(pZB5).

Another object yet still of the present invention is to provide a process for use of the recombinant strain ATCC31821/pZB5 to ferment 12% glucose and 3% xylose at about pH=5.5 and about 30° C. that utilizes xylose nearly completely (96%) in about 71 hours to obtain about a 45% increase of fermentation performance of xylose compared to the previous strain CP4 (pZB5) under the same condition, thus resulting in a 9% increase of the ethanol process yield; and to also provide a 37% increase in xylose sugar up take rate using Zymomonas strain ATCC31821/pZB5 compared to the previous strain CP4(pZB5).

A still further object of the present invention is to provide a biofuel comprising a mixture of ATCC31821/pZB5 and ethanol.

BRIEF DESCRIPTION OF THE DRAWINGS

FIG. 2 generally shows comparative graphs of fermentation profiles of Z. mobilis CP4(pZB5) and ATCC31821/pZB5 in RM containing 5% xylose or 1.5% glucose and 3.5% xylose supplemented with 20 µg/ml of Tc at 30° C. without pH control.

FIG. 3 generally shows comparative graphs of fermentation profiles of Z. mobilis CP4 (pZB5) and ATCC31821/pZB5 in RM containing 5% xylose or 1.5% glucose and 3.5% xylose supplemented with 20 µg/ml of Tc at 37° C. without pH control.

FIG. 4 shows comparative graphs of fermentation profiles of Z. mobilis CP4 (pZB5) and ATCC31821/pZB5 in MRM containing 12% glucose and 3% xylose supplemented with 20 µg/ml of Tc at 30° C. at pH 5.5.

DESCRIPTION OF THE PREFERRED EMBODIMENTS

In general, the method of making Zymomonas strains from Zymomonas mobilis strain ATCC31821 or its derivative is accomplished by: a) transforming an appropriate host strain suitable for preparation of DNA for transformation of ATCC31821 or its derivative with plasmid DNA; b) preparation of the DNAs from said host; c) transforming the ATCC31821 strain or its derivative with the DNA prepared from step b); and d) selecting the transformants using a selection marker and/or analyze correct size of the DNA from said transformants.

The process may proceed where the host is methylation deficient, and the methylation deficient host may be defective in DNA cytosine methylation (dcm$^-$) and/or DNA adenine methylase (dam$^-$).

As mentioned above, one preferred aspect of the present invention provides recombinant Zymomonas containing functional exogenous genes encoding xylose isomerase (XI), xylulokinase (XK), transaldolase (TAL) and transketolase (TKT), which represents an improvement for fermentation of xylose or a mixture of glucose and xylose upon prior-reported recombinant xylose-fermenting Zymomonas strains.

In general, recombinant Zymomonas can effectively ferment xylose, or a mixture of glucose and xylose to ethanol has been reported (Picataggio et al., U.S. Pat. No. 5,514,583). The recombinant Zymomonas made in the publication were accomplished by cloning of exogenous genes of XI, XK, TAL and TKT on a shuttle vector, following by using the resulting plasmid, pZB4 or pZB5, to transform Z. mobilis CP4 strain. The expression of the genes of XI, XK, TAL and TKT were under the control of at least one promotor recognized by Zymomonas. The transformed recombinant Z. mobilis CP4 containing added XI, XK, TAL and TKT genes can ferment xylose or a mixture of both glucose and xylose in contrast to the control strain containing the shuttle vector alone which only fermented the glucose alone (Picataggio et al., U.S. Pat. No. 5,514,583).

However, the recombinant xylose-fermenting Z. mobilis CP4 strains, for example, CP4/pZB5, fermented xylose at a slow rate, and substantial xylose was left unfermented under conditions when using a mixture of a total of 5% of glucose and xylose without pH control (where pH drops to about 4.5 towards end of the fermentation) or when using a mixture of a total of 12% of glucose and xylose at pH 5.5 at about 30° C. and 37° C. (FIGS. 2A, 2C, 3A, 3C and 4A). The slow xylose utilization rate and unfermented xylose resulted in low ethanol productivities and low ethanol process yields. Ethanol yields and productivities are two of the most important parameters effecting the cost of ethanol production from agricultural and cellulosic biomass.

It is more desirable to operate the industrial biomass-to-ethanol fermentation processes under low pH or without pH control to prevent bacterial contamination or reduce the cost of base addition using high concentrations of sugars. It is also more desirable to have such processes operated at higher temperatures to reduce the cooling cost during fermentation. In some of the biomass to ethanol conversion processes, glucose is hydrolyzed from cellulose by addition and action of the cellulase enzymes, and the soluble sugars, both glucose and xylose, are then converted to ethanol by a microorganism. Such processes are also referred to as a simultaneous saccharification and co-fermentation (SSCF) process. Cellulases required to hydrolyze the cellulose often prefer high temperatures for maximizing the cellulose hydrolysis rate. It is advantageous to have fermentation organisms operate at high temperatures. The present invention provides a recombinant xylose-fermenting Zymomonas strain with significant improvement in fermenting xylose or a mixture of glucose and xylose to ethanol under the above commercially desirable conditions.

Figure 1:
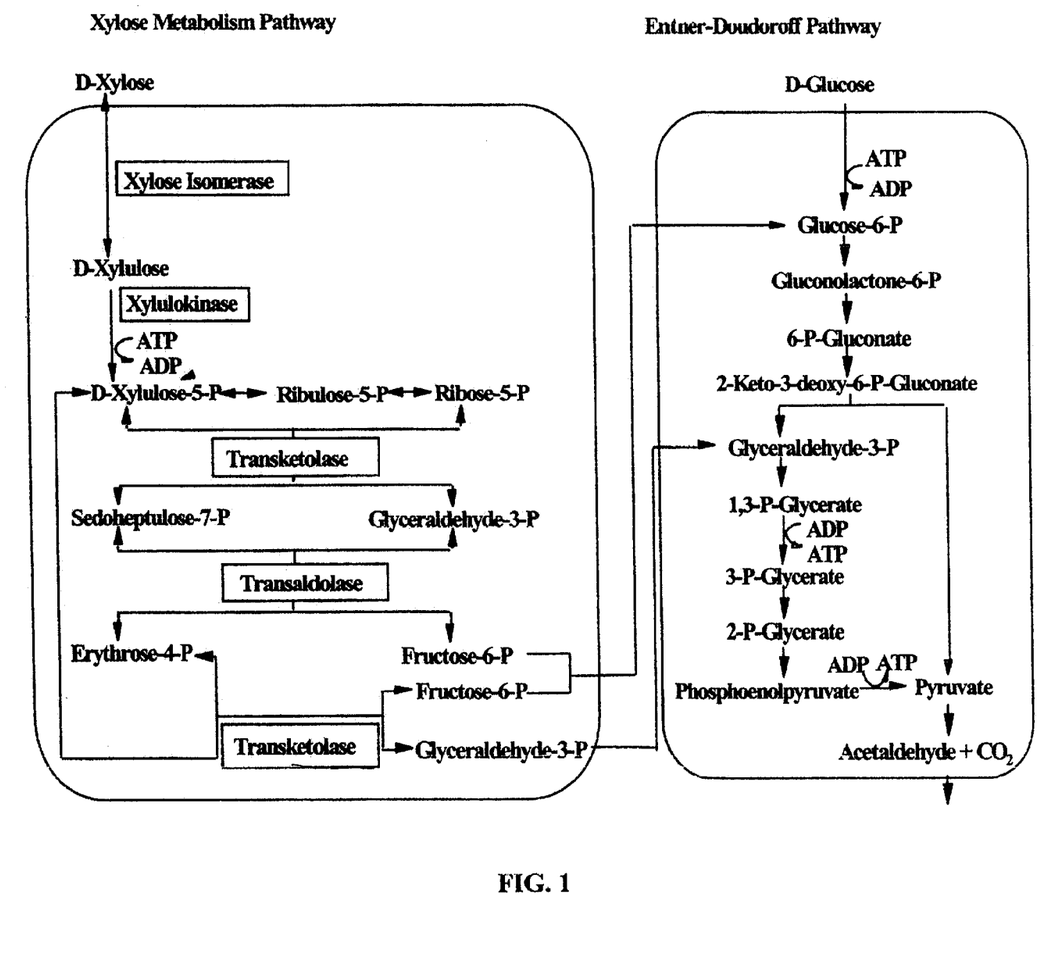
FIG. 1 generally shows a schematic of the pathways required to enable Z. mobilis to ferment xylose, i.e., the xylose metabolism pathway and the Entner-Doudoroff Pathway.

The pathway required to enable *Z. mobilis* to ferment xylose, namely the xylose metabolism pathway and the Entner-Doudoroff pathway is set forth in FIG. 1. The microorganism used to prepare the invention are those which are capable of being genetically altered to produce the necessary enzymes to form a metabolic pathway for catabolizing pentose sugars, particularly xylose. The microorganism may naturally have some enzymes in the pathway but is not able to ferment xylose into ethanol until it has been genetically altered.

The manner of genetic alteration may use any combination of known genetic engineering techniques such as mutation and addition of foreign DNA, provided that the microorganism is able to ferment pentose sugars to ethanol after treatment. Foreign DNA may be introduced into the microorganism by any conventional transformation technique such as conjugation, protoplast/competent cell transformation, transduction or electroporation. The preferred transformation method is electroporation.

Some *Z. mobilis* strains which are capable of fermenting hexoses to ethanol may be more difficult to be genetically manipulated than others because of their different genetic make-ups. Applicant has discovered that some of the *Z. mobilis* strains cannot be transformed easily or never be able to be transformed by foreign DNA but others do. One cannot predict the outcomes until transformation is attempted of the specific strains.

To attempt to obtain better xylose-fermenting *Z. mobilis* strains, applicant has tried to transform a number of *Z. mobilis* strains with the shuttle vector plasmid, pZB186, which was used to construct the xylose-fermenting plasmids, pZB4 and pZB5. The strains which demonstrated to be transformable by the vector plasmid were then transformed using the xylose-fermenting plasmids. While several xylose-fermenting Zymomonas strains were obtained, only one strain, ATCC31821/pZB5, demonstrated superior fermentation performance, which was the only strain obtained using ATCC31821 as a host after numerous trial of transformation by electroporation using a modified method, despite both plasmids being used to transform the strain. The transformation frequency of ATCC31821 using plasmid DNAs prepared from an ordinary *E. coli* host DH5 α that is often used to prepare plasmid DNAs for various genetic manipulation, was extremely low. The modified method with at least 100-fold increase in transformation frequency for ATCC31821 strain includes: 1) preparation of the plasmid DNAs from the *Z. mobilis* host, and 2) transformation of the ATCC31821 strain with the DNA prepared from step 1), and 3) finally selecting the transformants using a selection marker, analyzing the correct size of the plasmid and test growth of the transformant in a medium containing xylose as sole carbon source. The preferred *Z. mobilis* host is CP4 or B14023.

More efficient transformation methods are needed to further manipulate the organism, such as to place the exogenous genes encoding XI, XK, TAL and TKT into the *Z. mobilis* genome, which is a more preferred method for introduction of exogenous genes of interest and maintaining the stability of a strain capable of fermenting glucose and xylose in the absence of selection marker.

Applicant discovered the transformation frequency of strain ATCC31821 can be enhanced about 40000-fold when using DNAs prepared from itself as compared an ordinary *E. coli* host DH5, suggesting that this strain has a strong restriction system that limits the up take of foreign DNA. It was further discovered that about 10-fold and 1000-fold increases of transformation frequency of strain ATCC31821 can be obtained when using plasmid DNAs prepared from a modification (methylation by EcoK)-deficient host *E. coli* HB 101 and a DNA cytosine methylase (dcm)- and DNA adenine methylase (dam)-deficient host *E. coli* JM110. This results clearly demonstrated that the ATCC31821 strain likes to up take demethylated DNA and suggested that the strain has restriction system(s) which restrict DNAs methylated by cytosine methylase and/or adenine methylase, and by the EcoK methylation or by any methylation. One would expect that even greater transformation frequency of strain ATCC 31821 can be achieved by using DNA prepared from a host with a combination of modification (EcoK)-deficient, and dcm- and dam-deficient or a host lacks any methylation mechanisms. The transformation frequency for strain ATCC31821 using DNA prepared from an ideal host can be reached as that obtained by using DNA from itself. This should not limit,the methods of the transformation.

Accordingly, in preferred aspects of the present invention, a method of transforming strain ATCC31821 using foreign DNA includes steps: 1) first to transform a host strain which is desirable for preparation DNA for transformation of ATCC31821; 2) preparation of the DNAs from the host, and 3) transforming the ATCC31821 strain with the DNA prepared from step 2), and 4) selecting the transformants using a selection marker and/or analyzing correct size of the DNA from the transformants. In a more preferred aspects of the present invention, the above method can be further followed by testing growth of the transformants in medium containing xylose as a sole carbon source and selecting cells that grow on xylose. The preferred hosts for preparation of DNAs for using transformation of the ATCC31821 strain is selected from *Z. mobilis* CP4 and B14023 and *E.coli* JM110 and HB101, more preferable *E. coli* JM110. The preferred selection marker is selected by resistance to tetracycline or chromphenical or capability of utilization and growth on sugars such as xylose or arabinose or mannose. The preferred method of transformation is electroporation.

The superior microorganism, with improved fermentation performance on xylose, and a mixture of glucose and xylose, according to the present invention may be mixed with xylose, or a combination of xylose and or other sugars contained in a medium to produce ethanol. The medium may include other fermentable sugars, such as glucose. The range of percentage with individual sugar in a mixture containing glucose, xylose and other sugars may vary from substrates to substrate. It is reasonable to expect that the microorganism according to the present invention can ferment a mixture of up to a total of 16% sugar to ethanol. If microbial growth is desired, other nutrients which are necessary for microbial growth may be added and the microorganism allowed to reproduce.

When the substrate is cellulosic material, the cellulose may be hydrolyzed to sugars simultaneously or separately and also fermented to ethanol. Since hemicellulose is generally easier to hydrolyze to sugars than cellulose, it is preferable to prehydrolyze the cellulosic material, separate the pentoses and then hydrolyze the cellulose by treatment with steam, acid, alkali, cellulases or combinations thereof to form glucose. Starch-hydrolyzing enzymes may be added to release glucose from residual starch in agricultural residues. Hexoses and pentoses may be fermented to ethanol simultaneously, sequentially, separately or together using the microorganism of the present invention. If so desired, the hexoses may be fermented to ethanol by a different microorganism than the pentoses, such as yeast, natural Zymomonas, etc.

Many fermentation conditions are known per se as shown by the references mentioned in the Background of the Invention section. Z. mobilis is a facultative anaerobic bacterium. It has theoretical yields of ethanol from sugar of up to 97% which provides for little microbial growth, if so desired. The optimum pH conditions range from about 3.5 to about 7.5. Substrate concentrations of up to about 25% (based on glucose), and under some conditions even higher, may be used. Unlike other ethanol producing microorganisms, no oxygen is needed at any stage for microorganism survival. Also unlike yeast, oxygen does not drastically reduce ethanol productivity or greatly increase cell growth. Agitation is not necessary but may enhance availability of substrate and diffusion of ethanol. Accordingly, the range of fermentation conditions may be quite broad. Likewise, any of the many known types of apparatus may be used for the present invention.

The microorganism according to the present invention may be used as a biologically pure culture or it may be used with other ethanol producing microorganisms in mixed culture. Microorganisms able to ferment xylose and arabinose can be cultured themself or can then be mixed with microorganisms able to ferment glucose. Biologically pure cultures are generally easier to optimize but mixed cultures may be able to utilize additional substrates. One may also add enzyme(s) to the fermentor to aid in the degradation of substrates or to enhance ethanol production. For example, cellulase may be added to degrade cellulose to glucose simultaneously with the fermentation of glucose to ethanol by microorganisms in the same fermentor. Likewise, a hemicellulase may be added to degrade hemicellulose.

In the preferred embodiment using a genetically engineered Zymomonas, cultures are found to be relatively resistant to contamination by other microorganisms. Nonetheless, it is preferred to eliminate or disable preexisting deleterious microorganisms in the substrate added to the Zymomonas culture.

After fermentation, the ethanol, which may achieve concentrations of up to about 13%, is separated from the fermentation broth by any of the many conventional techniques known to separate ethanol from aqueous solutions. These methods include evaporation, distillation, solvent extraction and membrane separation. Particles of substrate or microorganisms may be removed before ethanol separation to enhance separation efficiency.

Once the fermentation is complete, excess microorganisms and unfermented substrate may be either recycled or removed in whole or in part. If removed, the microorganisms may be killed, dried or otherwise treated. This mixture may be used as animal feed, fertilizer, burnt as fuel or discarded.

While the discussion of the fermentation in this specification generally refers to a batch process, parts or all of the entire process may be performed continuously. To retain the microorganisms in the fermentor, one may separate solid particles from the fluids. This may be performed by centrifugation, flocculation, sedimentation, filtration, etc. Alternatively, the microorganisms may be immobilized for retention in the fermentor or to provide easier separation.

Unless specifically defined otherwise, all technical or scientific terms used herein have the same meaning as commonly understood by one of ordinary skill in the art to which this invention belongs. Although any methods and materials similar or equivalent to those described herein can be used in the practice or testing of the present invention, the preferred methods and materials are better illustrated by the use of the following non-limiting examples. The following examples are offered by way of illustration, and not by way of limitation.

The pathways required to enable Z. mobilis to ferment xylose, namely, the xylose metabolism pathway and the Entner-Doudoroff Pathway is set forth in FIG. 1.

The transformation of the xylose-germenting plasmids to Z. mobilis strains ATCC31821 (ZM4), ATCC39676, and NRRL B14023 are shown in Example 1.

EXAMPLE 1

Xylose-fermenting Z. mobilis was developed by transformation of the strain of Z. mobilis CP4 using plasmids, pZB5 and pZB4, which contains four xylose-metabolizing genes (Picataggio et al., U.S. Pat. No. 5,514,583). To attempt to obtain better xylose-fermenting Z. mobilis, several other Z. mobilis strains, ATCC31821, ATCC39676, and NRRL B 14023 were tested to see whether these strains can be transformed by the vector plasmid, pZB186, which was used to construct xylose-fermenting plasmids. The plasmid DNA of pZB186 was prepared from the strain of E. coli DH5α. An electroporation procedure described previously (Picataggio et al., U.S. Pat. No. 5,514,583) was used for transformation. The electroporation was carried out in approximately $10^9$ cells/ml with about 2 $\mu$g DNA in 40 $\mu$l of 10% (w/v) glycerol at 16 kv/cm, 200$\Omega$ and 25$\mu$F. After electroporation, the cells were allowed to recover at 30° C. for 3–16 hours in a liquid medium (mating medium) comprised of 5% glucose, 10% yeast extract (Difco), 5% Tryptone (Difco), 0.25% ammonium sulfate, 0.02% potassium phosphate, dibasic and 1 mM magnesium sulfate. Transformants containing pZB186 arose in the same medium additionally containing 1.5% agar and tetracycline (Tc) (20 $\mu$g/ml) (mating plate) following anaerobic incubation at 30° C. for 2 or more days. The transformation frequency was calculated by CFU (number of transformants)/$\mu$g DNA. Strains ATCC39676 and NRRL B14023 were transformed at a relative high frequency (about 2 to 6×$10^3$ CFU/$\mu$g DNA) while strain ATCC31821 was transformed at a very low frequency (about 1 CFU/$\mu$g DNA or less).

The xylose-fermenting plasmids, pZB4 and pZB5, were used to transform strains ATCC39676 and NRRL B14023 by electroporation. Although the transformation frequency of these two strains using the xylose-fermenting plasmids was reduced dramatically as compared to the vector plasmid, several transformants of 39676/pZB4, 39676/pZB5, B14023/pZB4 and B14023/pZB5 were obtained by isolating the tetracycline resistant colonies from the mating plates.

However, restriction analyses of the plasmid DNA from tetracycline-resistant transformants revealed that only a few transformants contained the correct plasmids. These transformants were further selected for their growth in a liquid RMX medium comprised of 2% xylose, 10% yeast extract (Difco) and 0.02% potassium phosphate with added tetracycline (20 μg/ml). The strains that grew well in the above medium were designated as 39676/pZB4, 39676/pZB5, B14023/pZB4 and B14023/pZB5 respectively. All the strains performed comparable to the prior art reported strain CP4/pZB5.

The same xylose-fermenting plasmids, pZB4 and pZB5, were used to transform strain ATCC31821. No transformant was obtained using DNA prepared from E. coli DH5α after more than ten trials of transformation. Several methods, including using various growth conditions, electroporating media and conditions were tried to improve the tranformability of strain ZM4. The best conditions yielded about 20 transformants/μg DNA of pZB186.

However, when using DNA purified from Z. mobilis CP4 or B14023 it was found that there was about a 100-fold increase of the transformation frequency. Consequently, plasmid DNAs of pZB4 and pZB5 were prepared from Z. mobilis CP4. A few Tc resistance transformants were obtained from 4–5 trials of transformation. But only smaller plasmids that resulted from deletion were detected by restriction analyses of the plasmid DNA from tetracycline-resistant ZM4 transformants. After more than ten trials of transformation using both pZB4 and pZB5, one Tc resistant ZM4 transformant was found to have the correct size of pZB5. Cells of this Tc resistant transformant was plated on RMX containing 20 μg/ml of Tc. Several colonies arose after incubation at 30° C. for four days. One of them exhibited the best fermentation performance of xylose to ethanol and was isolated and designated as 31821/pZB5.

EXAMPLE 2

Figure 2A:
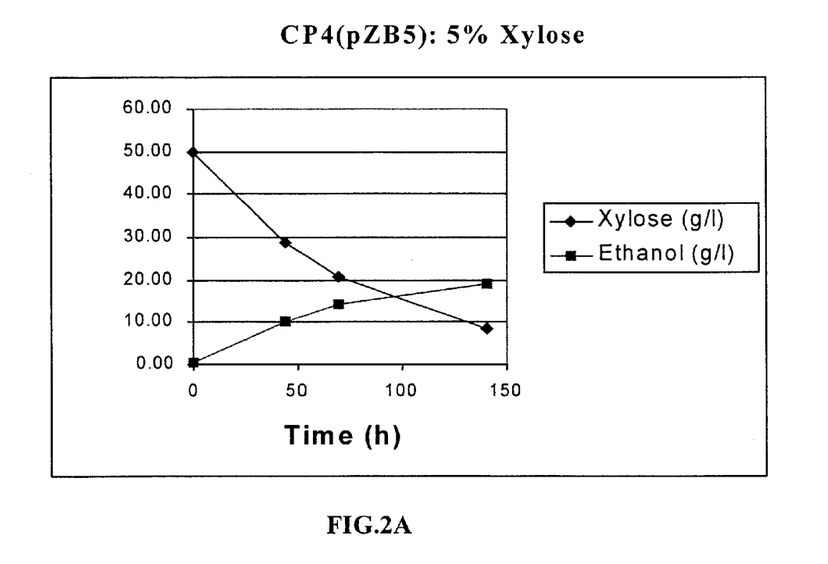
FIGS. 2A and 2B specifically show fermentation profiles of Z. mobilis CP4 (pZB5) and ATCC31821/pZB5 on a comparative basis for 5% xylose.
Figure 2B:
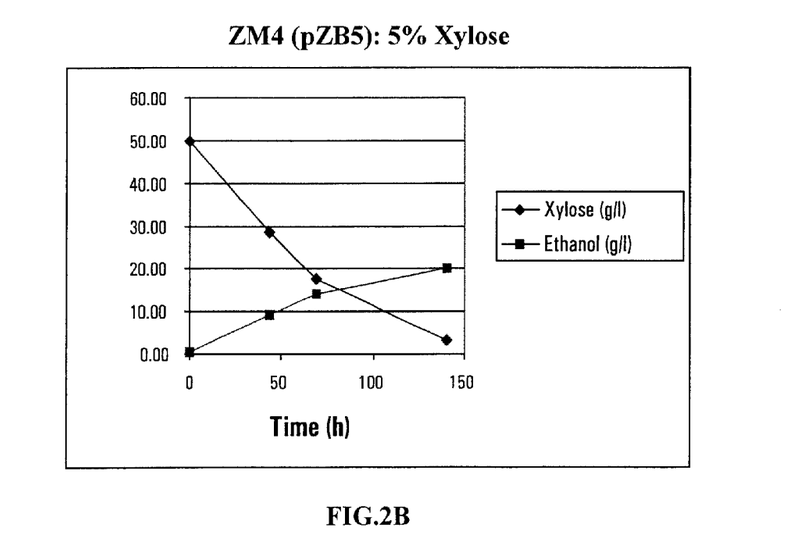

The fermentation performance of the xylose-fermenting strains obtained above were evaluated in RM medium comprised of 1% (w/v) yeast extract (Difco), 0.2% potassium phosphate, dibasic and 5% of xylose supplemented with 20 μg/ml of Tc at 30° C. without pH control. The Z. mobilis CP4 (pZB5) was used as a control strain. Samples were taken periodically for analysis of residual sugars and product formation on HPLC. The average volumetric productivity, average sugar up take rate, percent of xylose utilization, the ethanol process yield and metabolic ethanol yield were calculated. Among the strains tested, ATCC31821/pZB5 demonstrated superior performance in xylose utilization. A comparison is made between the previously studied Z. mobilis CP4(pZB5) and ATCC31821/pZB5. The test results are shown in FIGS. 2A and 2B.

The average volumetric productivity and sugar up take rate over the exponential phase of growth, the overall xylose utilization rate and ethanol process yield are calculated in Table 1, where there is a comparison of fermentation performance of Z. mobilis CP4 (pZB5) and ATCC31821/pZB5 in RM containing 5% xylose supplemented with 20 μg/ml of Tc at 30° C. without pH control.

TABLE 1

|  | CP4 (pZB5) | ATCC31821/ pZB5 | Ratio ATCC31821/ pZB5 vs CP4 (pZB5) |
|---|---|---|---|
| Qp, ave (g/l/h) | 0.21 | 0.19 | 0.91 |
| Qs, xyl, ave (g/l/h) | 0.48 | 0.48 | 1.01 |
| Xylose utilization rate (%) | 83 | 93 | 1.12 |
| Yp (%) | 73 | 77 | 1.05 |

Qp, ave (g/l/h) = the average volumetric productivity over the exponential phase of growth (grams of ethanol produced per liter per hour).
Qs, xyl, ave (g/l/h) = the average up take rate of xylose over the exponential phase of growth (grams of sugar utilized per liter per hour).
Xylose utilization rate (%) = overall percent of xylose utilized (residual xylose concentration at the end of the fermentation / initial xylose concentration × 100).
Yp (%) = ethanol process yield (grams of ethanol produced / grams of initial available sugars × 100).

As can be seen from the above data, there was a 12% increase in utilization of xylose and a 5% increase in ethanol process yield using Zymomonas strain ATCC31821/pZB5 compared to the previous strain CP4 (pZB5). Both strains have comparable average volumetric activity and average up take rates of xylose.

EXAMPLE 3

Figure 2C:
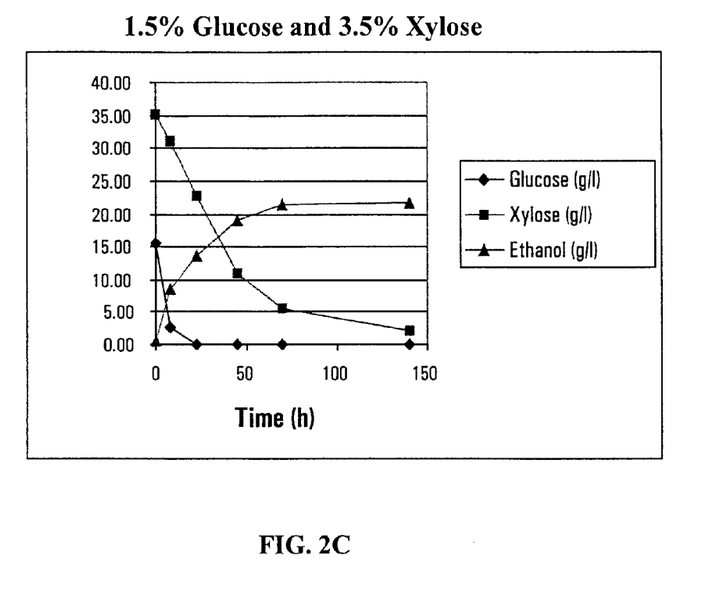
FIGS. 2C and 2D show fermentation profiles of CP4 (pZB5) and ATCC31821/pZB5 at 30° C. without pH control for 1.5% glucose and 3.5% xylose on a comparative basis.
Figure 2D:
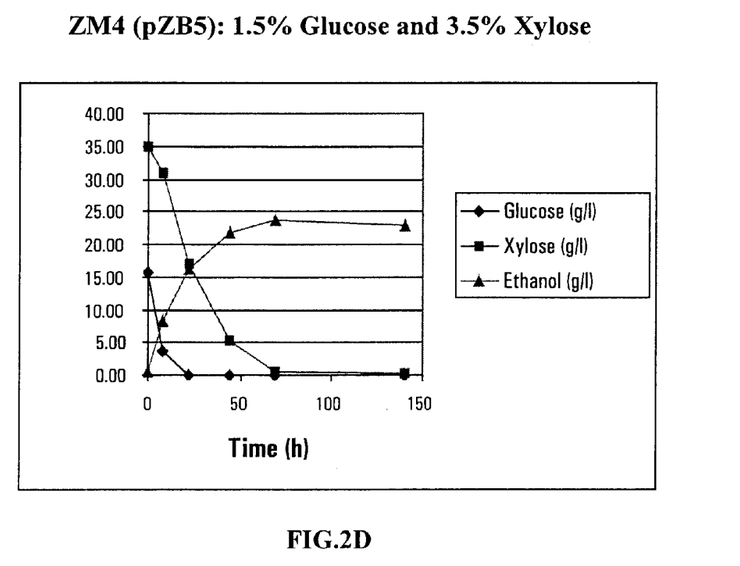

Same as Example 2, except that a mixture of 1.5% glucose and 3.5% xylose were used in lieu of 5% xylose. A comparison is made between previously studied Z. mobilis CP4 (pZB5) and ATCC31821/pZB5. The test results are shown in FIGS. 2C and 2D.

The average volumetric productivity and sugar up take rate over the exponential phase of growth, the overall xylose utilization rate and ethanol process yield are calculated in TABLE 2, which is a comparison of fermentation performance of Z. mobilis CP4(pZB5) and ATCC31821/pZB5 in RM containing 1.5% glucose and 3.5% xylose supplemented with 20 μg/ml of Tc at 30° C. without pH control.

TABLE 2

|  | CP4 (pZB5) | ATCC31821/ pZB5 | Ratio ATCC31821/ pZB5 vs CP4 (pZB5) |
|---|---|---|---|
| Qp, ave(g/l/h) | 0.59 | 0.71 | 1.20 |
| Qs, xyl, ave (g/l/h) | 0.55 | 0.82 | 1.49 |
| Qs, glu/xyl,ave (g/l/h) | 1.26 | 1.53 | 1.21 |
| Xylose utilization rate (%) | 84 | 99 | 1.18 |
| Yp (%) | 81 | 90 | 1.12 |

Qs, glu/xyl,ave (g/l/h) = the average up take rate of xylose and glucose over the exponential phase of growth (grams of sugar utilized per liter per hour).

As can be seen from the above data, there was an 18% increase in utilization of xylose and a 12% increase in ethanol process yield using Zymomonas strain ATCC31821/pZB5 compared to the previous strain CP4 (pZB5). There was also a 20% increase in average volumetric productivity, a 49% increase in xylose sugar up take rate and a 21% increase in total sugar up take rate using Zymomonas strain ATCC31821/pZB5 compared to the previous strain CP4 (pZB5).

EXAMPLE 4

Figure 3A:
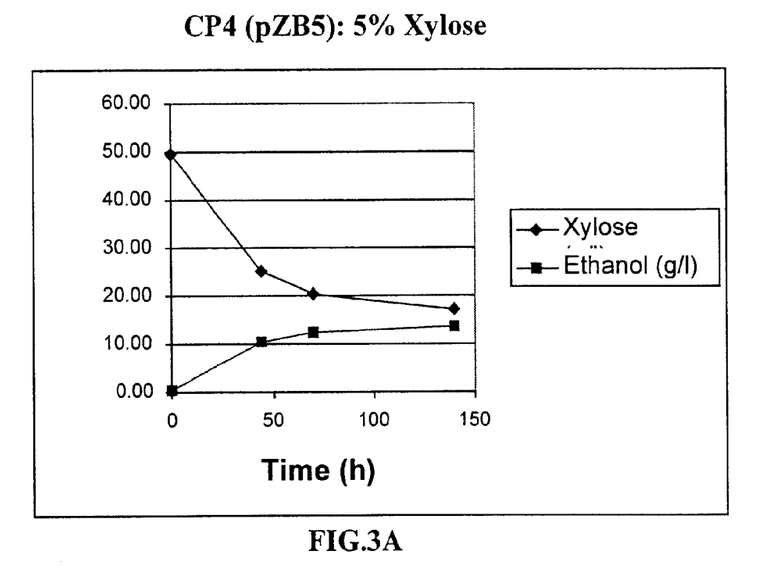
FIGS. 3A and 3B show fermentation profiles of Z. mobilis CP4 (pZB5) and ATCC31821/pZB5 at 37° C. without pH control on a comparative basis for 5% xylose.
Figure 3B:
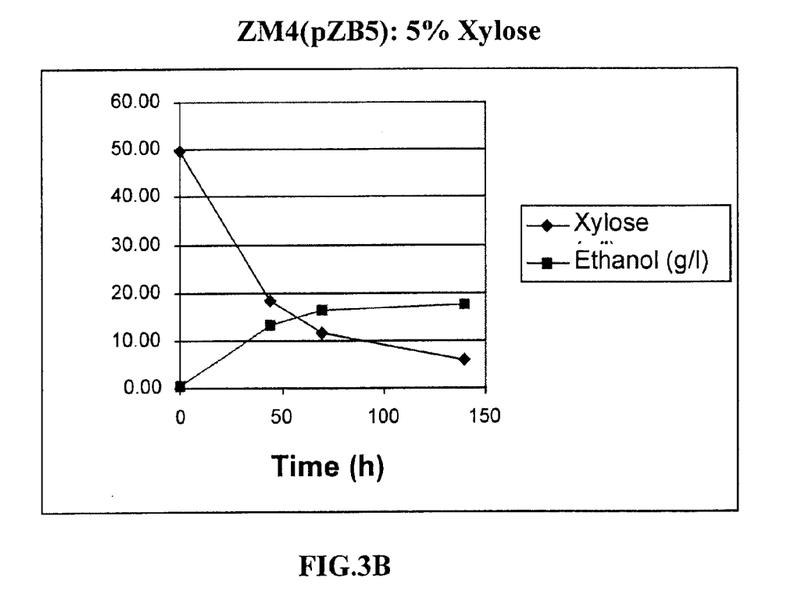

Same as Example 2, except that a temperature of 37° C. was used in lieu of 30° C. A comparison is made between the previously studied Z. mobilis CP4 (pZB5) and ATCC31821/pZB5. The test results are shown in FIGS. 3A and 3B.

The average volumetric productivity and sugar up take rate over the exponential phase of growth, the overall xylose utilization rate and ethanol process yield are calculated in TABLE 3, which is a comparison of fermentation performance of Z. mobilis CP4 (pZB5) and ATCC31821/pZB5 in RM containing 5% xylose supplemented with 20 μg/ml of Tc at 37° C. without pH control.

TABLE 3

|  | CP4 (pZB5) | ATCC31821/ pZB5 | Ratio/ ATCC31821/ pZB5 vs CP4 (pZB5) |
|---|---|---|---|
| Qp,ave(g/l/h) | 0.23 | 0.28 | 1.25 |
| Qs, xyl, ave (g/l/h) | 0.56 | 0.71 | 1.28 |
| Xylose utilization rate (%) | 65 | 88 | 1.34 |
| Yp (%) | 52 | 66 | 1.28 |

As can be seen from the above data, there was a 34% increase in utilization of xylose and 28% increase in the ethanol process yield using Zymomonas strain ATCC31821/pZB5 compared to the previous strain CP4 (pZB5). There was also a 25% increase in average volumetric productivity and a 28% increase in xylose sugar up take using the Zymomonas strain ATCC31821/pZB5 compared to the previous strain CP4 (pZB5).

EXAMPLE 5

Figure 3C:
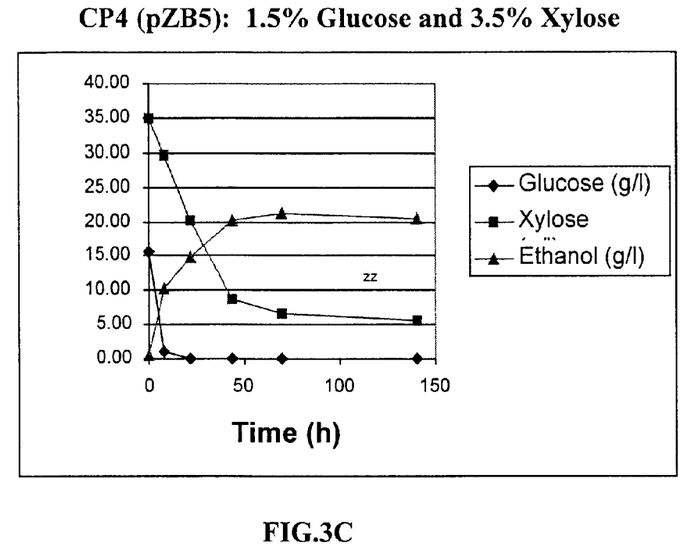
FIGS. 3C and 3D show fermentation profiles of Z. mobilis CP4 (pZB5) and ATCC31821/pZB5 at 37° C. without pH control for 1.5% glucose and 3.5% xylose on a comparative basis.
Figure 3D:
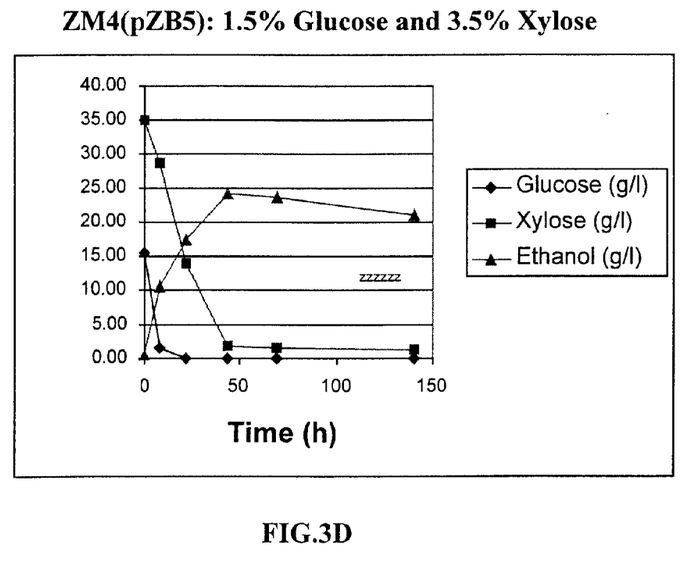

Same as Example 3, except that a temperature of 37° C. was used in lieu of 30° C. A comparison is made between the previously studied Z. mobilis CP4 (pZB5) and ATCC31821/pZB5. The test results are shown in FIGS. 3C and 3D for a sugar mixture of 1.5% glucose and 3.5% xylose.

The average volumetric productivity and sugar up take rate over the exponential phase of growth, the overall xylose utilization rate and ethanol process yield are calculated in Table 4, which is a comparison of fermentation performance of Z. mobilis CP4 (pZB5) and ATCC31821/pZB5 in RM containing 1.5% glucose and 3.5% xylose supplemented with 20 μg/ml of Tc at 37° C. without pH control.

TABLE 4

|  | CP4 (pZB5) | ATCC31821/ pZB5 | Ratio ATCC31821/ pZB5 vs CP4 (pZB5) |
|---|---|---|---|
| Qs, xyl, ave (g/l/h) | 0.68 | 0.96 | 1.40 |
| Qs, glu/xyl,ave (g/l/h) | 1.39 | 1.67 | 1.20 |
| Xylose utilization rate (%) | 81 | 96 | 1.18 |
| Yp (%) | 79 | 89 | 1.13 |

As can be seen from above data, there was an 18% increase in utilization of xylose and a 13% increase in ethanol process yield using Zymomonas strain ATCC31821/pZB5 compared to the previous strain CP4 (pZB5). There was also an 18% increase in the average volumetric productivity and a 40% increase in xylose sugar up take rate and a 20% increase total sugar up take rate using Zymomonas strain ATCC31821/pZB5 compared to the previous strain CP4 (pZB5).

EXAMPLE 6

A further comparison between the previous Z. mobilis strain CP4(pZB5) and ATCC31821/pZB5 in MRM media comprised of 0.5% (w/v) yeast extract (Difco), 0.1% $(NH_4)_2SO_4$, 0.2% $KH_2PO_4$, 0.1% $MgSO4.7H_2O$ containing 15% sugar (12%glucose and 3% xylose) supplemented with 20 μg/ml of Tc at pH5.5 and 30° C. was run and the results are shown in FIG. 4 and Table 5, in which Table 5 is a comparison of fermentation performance of Z. mobilis CP4 (pZB5) and ATCC31821/pZB5 in MRM containing 12% glucose and 3% xylose supplemented with 20 μg/ml of Tc at 30° C. and pH=5.5.

Figure 4A:
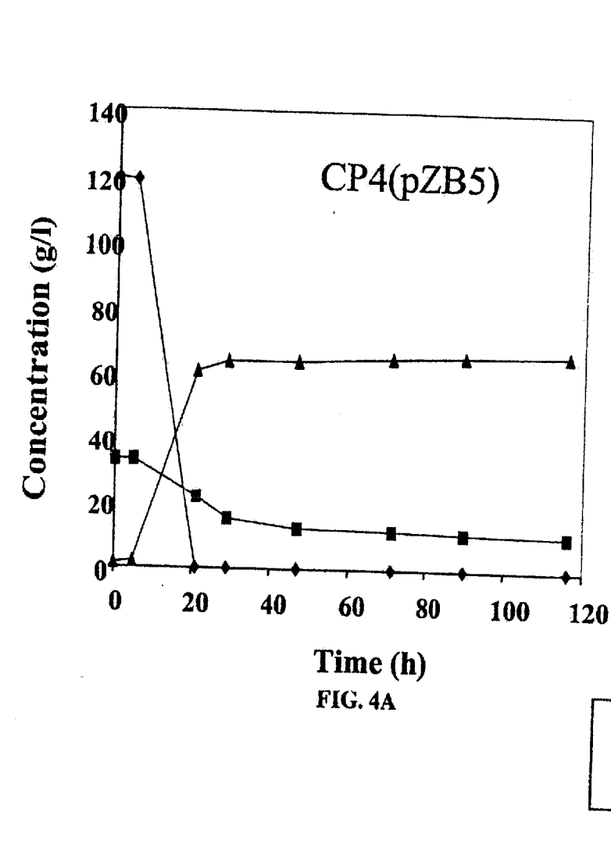
FIG. 4A shows the fermentation profile of Z. mobilis CP4 (pZB5) in a 12% glucose and 3% xylose sugar mixture at pH 5.5 and 30° C.
Figure 4B:
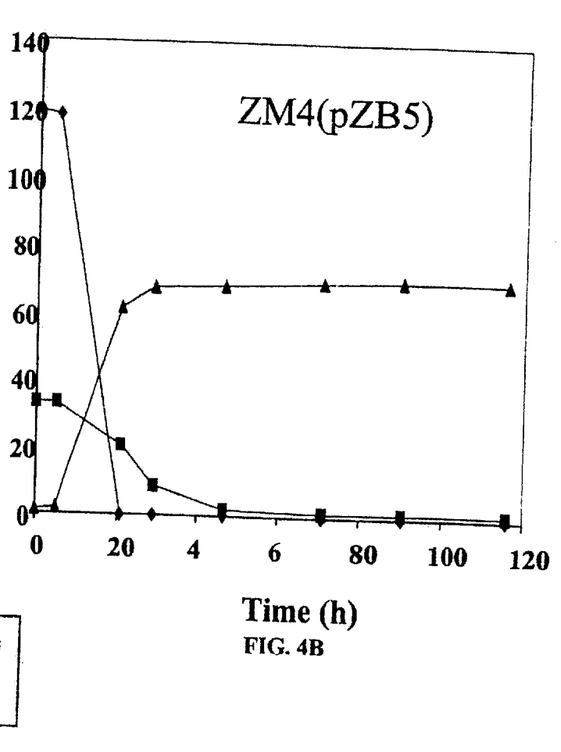
FIG. 4B shows the fermentation profile of ATCC31821/pZB5 in a 12% glucose and 3% xylose sugar mixture at pH 5.5 and 30° C.

More specifically, FIG. 4A shows the fermentation of Z. mobilis CP4 (pZB5) and FIG. 4B shows the fermentation profile for ATCC31821/pZB5.

TABLE 5

|  | CP4 (pZB5) | ATCC31821/ pZB5 | Ratio ATCC31821/ pZB5 vs CP4 (pZB5) |
|---|---|---|---|
| Qp, ave (g/l/h) | 2.83 | 2.87 | 1.01 |
| Qs, xyl, ave (g/l/h) | 0.62 | 0.85 | 1.37 |
| Qs, glu/xyl,ave (g/l/h) | 6.25 | 6.30 | 1.01 |
| Xylose utilization rate (%) | 66 | 96 | 1.45 |
| Yp (%) | 82 | 89 | 1.09 |

As can be seen from above data, there was an 45% increase in utilization of xylose and a 9% increase in ethanol process yield using Zymomonas strain ATCC31821/pZB5 compared to the previous strain CP4 (pZB5). There was also a 37% increase in xylose sugar up take rate using Zymomonas strain ATCC31821/pZB5 compared to the previous strain CP4 (pZB5).

A method of increasing transformation frequency of Z. mobilis ATCC31821 is shown in Example 7.

EXAMPLE 7

The xylose-fermenting Z. mobilis ATCC31821 recombinant strain exhibits superior characteristics for fermentation of glucose and xylose to ethanol. It is very critical to improve the transformation frequency so that it can be genetically manipulated easily. The transformation frequency was improved about 10-fold by various growth conditions, electroporating media and conditions. Using DNA from Z. mobilis CP4 improved the transformation frequency about 100-fold. However, it is still very difficult to obtain recombinant xylose-fermenting transformants using the above methods as shown in Example 1.

When using DNA prepared from ATCC31821 the transformation frequency of $4 \times 10^4$ CFU/μg DNA for ATCC31821 was obtained which is about a 40000-fold increase as compared to DNA prepared from a widely used host E. coli DH5α. This suggests that the ATCC31821 strain has a strong restriction system that limits up take of foreign DNA. To test this hypothesis plasmid DNAs of pZB186 were prepared from E. coli strains with various genetic backgrounds and were used to transform ATCC31821 using a standard procedure.

As shown in Table 6, the transformation frequency was very low when using plasmid DNAs of pZB186 prepared from DH5α and C600. About 10-fold higher transformation frequency was obtained when using plasmid DNA from HB101. However, using a plasmid DNA of pZB186 prepared from JM110 resulted in more than a 1000-fold increase of the transformation frequency as compared to DNA prepared from DH5α. HB101 is a modification-deficient (EcoK) host and JM110 is defective in DNA cytosine methylase (dcm) and DNA adenine methylase (dam). Using DNA without the EcoK modification (methylation) the transformation frequency was increased by about 10-fold and using DNA without the dcm- and/or dam-methylation the transformation frequency was increased by more than 1000-fold. The above results clearly show that ATCC31821 likes to accept demethylated DNA and suggest that ATCC31821 has restriction system(s) which restrict DNAs methylated by cytosine methylase and/or adenine methylase, and by the EcoK methylation system or by any methylation.

One would expect that even a greater transformation frequency for ATCC31821 can be achieved by using DNA prepared from a host with a combination of modification (EcoK)-deficient, and dcm- /dam-deficient or a host which lacks any methylation mechanism. In theory the transformation frequency for ATCC31821 using DNAs from such host can be reached as high as that obtained by using DNA from ATCC31821 strain.

TABLE 6

| Host Strain | Genetic Background | Trans. frequency CFU/µg DNA (pZB186) |
|---|---|---|
| DH5α | hsdR17 ($r^-m^+_K$) | 1 |
| HB101 | hsdS20 ($r^-m^-_B$) mcrB$^-$mrr$^-$ | 13 |
| C600 | (dcm$^+$dam$^+$ M$^+$) | 1 |
| JM110 | dcm$^-$dam$^-$ | 1300 |

Using plasmids such as pZB4 or pZB5 prepared from JM110, Z. mobilis ATCC31821 transformants can be routinely obtained per one transformation experiment. This method greatly enhanced the capability of genetic manipulation including transformation and gene integration in ATCC31821. One would expect that high transfection/transconjugation frequency could be obtained for introduction of foreign DNAs to ZM4 by transconjugation or transfection using hosts with demethylation as a DNA donor. Furthermore, strains with dcm$^-$ and/or dam$^-$ and/or other similar genetic background of JM110 should be able to be used as a host (or donor) for introducing DNAs into ATCC31821 resulting in similar results.

I claim:

1. A *Zymomonas mobilis* strain ATCC31821/pZB5 capable of producing ethanol upon fermentation of a carbohydrate medium containing xylose to provide enhanced xylose utilization and enhanced ethanol process yield, said strain comprising exogenous genes encoding xylose isomerase, xylulokinase, transaldolase and transketolase, said genes are fused to at least one promotor recognized by Zymomonas which regulates the expression of at least one of said genes.

2. A process for production of ethanol from fermentable carbohydrate substrate medium comprising culturing in the medium without pH control, a strain of *Zymomonas mobilis* ATCC31821/pZB5 which is characterized by ethanol productivity at a temperature range of from about 25 to about 45° C. and utilizes about 99% of xylose to effect a fermentation reaction to provide improved yields of ethanol, and recovering the ethanol so produced.

3. The process of claim 2 wherein said temperature is from about 30° C. to about 37° C.

4. The process of claim 3, wherein the fermentable carbohydrate substrate is xylose.

5. The process of claim 3, wherein the fermentable carbohydrate substrate is a mixture of glucose and xylose.

6. The process of claim 5, wherein glucose is present in about 1.5% and xylose is present in about 3.5%.

7. The process of claim 6, wherein said fermentation reaction is carried out for about 69 hours.

8. The process of claim 4, wherein xylose is present in an amount of 5%.

9. A process for production of ethanol from a medium containing a fermentable carbohydrate substrate medium comprising culturing in the medium at a pH range of from about 4.5 to about 6.5 a strain of *Zymomonas mobilis* ATCC31821/pZB5 at a temperature range of from about 25 to about 45° C. and utilizes about 96% of xylose to effect a fermentation reaction to provide improved yields of ethanol, and recovering the ethanol produced.

10. The process of claim 9 wherein said pH is about 5.5 and said temperature is about 30° C.

11. The process of claim 10 in which said fermentable carbohydrate substrate is a mixture of glucose and xylose.

12. The process of claim 11 in which said glucose is present in an amount of about 12% by weight and said xylose is present in an amount of about 3% by weight.

13. A composition comprising a combination of a mixture of ATCC31821/pZB5 and ethanol.

* * * * *